United States Patent [19]

Bejarano

[11] 4,263,682

[45] Apr. 28, 1981

[54] SELF-SEALING VALVE AND FLUID FILLABLE ARTICLE INCLUDING SUCH A VALVE

[75] Inventor: Mark A. Bejarano, Midland, Mich.

[73] Assignee: Dow Corning Corporation, Midland, Mich.

[21] Appl. No.: 939,038

[22] Filed: Sep. 1, 1978

[51] Int. Cl.³ .......................... A61F 1/24; A41C 3/10; F16K 15/20
[52] U.S. Cl. .................................... 3/36; 137/223; 128/462; 46/90; 273/65 D
[58] Field of Search .............. 3/36; 137/223; 128/462; 46/87, 90; 273/65 C, 65 D

[56] References Cited

U.S. PATENT DOCUMENTS

| | | | |
|---|---|---|---|
| 1,910,961 | 5/1933 | Perry | 137/223 |
| 2,142,414 | 1/1939 | Riddell | 273/65 D |
| 2,151,466 | 3/1939 | Eken | 137/223 |
| 2,568,976 | 9/1951 | Andrews | 137/223 |
| 2,597,924 | 5/1952 | Davenport et al. | 128/462 |
| 2,697,229 | 12/1954 | Krueger | 128/462 |
| 3,523,563 | 8/1970 | Mirando | 46/90 X |
| 3,600,718 | 8/1971 | Boone | 3/36 |
| 4,178,643 | 12/1979 | Cox, Jr. | 3/36 |

FOREIGN PATENT DOCUMENTS 639593 6/1950 United Kingdom .................. 46/90

OTHER PUBLICATIONS

Silastic Varifil Mammary Implant, Dow Corning Bulletin 51-358, dated Oct. 1977, (4 p. pamphlet), 3-36.

Primary Examiner—Ronald L. Frinks
Attorney, Agent, or Firm—Max J. Kenemore

[57] ABSTRACT

A self-sealing valve useful in a fluid fillable article, such as a mammary prosthesis, includes first and second planar members which are bonded together so as to leave an elongated unbonded portion therebetween. Openings are formed for communication between the unbonded portion and the inside and outside of a fluid fillable article containing the valve. The openings are offset from one another so that the openings and the unbonded portion form a normally open channel through the valve. At least one planar member is sufficiently flexible to close the channel responsive to pressure from within a fluid fillable member containing the valve.

17 Claims, 8 Drawing Figures

SELF-SEALING VALVE AND FLUID FILLABLE ARTICLE INCLUDING SUCH A VALVE

BACKGROUND OF THE INVENTION

Field of the Invention

This invention relates generally to valves and more specifically to self sealing valves for use in fluid fillable articles such as mammary prostheses.

Background of the Invention

Self sealing valves of various types for use with fluid fillable articles are known. However, previously known valves have been relatively bulky and relatively complicated to construct.

Bulky valves are not desirable in certain applications. For example, it is undesirable to include palpable valves in a mammary prothesis.

Valves which are complicated to construct are usually undesirably expensive. Such valves often have a multiplicity of parts, causing them to be bulky as well as expensive.

One valve exemplary of the prior art is disclosed in U.S. Pat. No. 2,697,229 to Krueger. That patent shows a flat tube which is inserted into an article and cemented to a wall of the article. The tube creates a passageway which leads directly from the interior of the article to the outside. The valve is useful in such articles as air-inflatable toys and external breast pads. The air pressure in the article keeps the tube closed and prevents deflation through the tube.

The valve of Krueger is manufactured by forming holes in the tube and then cementing the tube to a wall of the article. During cementing, the tube is held flat against the wall by a jig and cement is inserted by a needle into the holes. The cement connects the internal wall of the tube to the wall of the article so that the tube is held in a flat position. The holes are located so as to create a passageway down the center of the tube.

U.S. Pat. No. 3,523,563 to Mirando shows a self sealing valve for air inflation of articles such as toys. Layers of a tacky material are forced apart to create a passageway into the article. A tube is placed in the passageway for inflation. Upon removing the tube, the valve closes and the layers adhere to one another because of the tackiness of the material and because of pressure from within the inflated article.

Another self sealing valve is supplied with gel fillable mammary prostheses which are commercially available from Dow Corning Corporation (Midland, MI 48640) under the tradename SILASTIC® Verifil Mammary Implant. The valves include a channel formed from a flexible material. The channel is closed by pressure of the gel within the prosthesis.

This valve has received wide commercial acceptance; however, it also presents opportunities for improvement. Primarily, improvements in the complicated manufacture of the valve are desirable. The valve includes disks which serve as collars around distal and proximal openings at either end of the valve channel. The disks and valve channel are supported on a mounting flange. A valve with fewer parts which must be assembled is desirable.

U.S. Pat. No. 3,600,718 to Boone shows a simpler valve. The valve disclosed by Boone is a body of highly viscous gel which flows to fill any opening left when a filler tube is removed from a mammary prosthesis.

SUMMARY OF THE INVENTION

It is therefore an object of the present invention to present a self sealing valve for use in fluid fillable articles.

It is also an object of this invention to furnish a self-sealing valve which is relatively simple and inexpensive to manufacture.

It is a further object of the invention herein described to provide a fluid fillable mammary prosthesis containing a self sealing valve which has reduced palpability upon surgical implantation.

It is still another object of this invention to make a self sealing valve for use in fluid fillable article.

It is yet a further object of this invention to make a fluid fillable mammary prosthesis containing a self sealing valve.

It is also an object of the present invention to overcome the disadvantages of the prior art.

These and other objects are accomplished by the present invention which comprises a valve for use in a fluid fillable article. The valve comprises, generally speaking, first and second members having planar surfaces which are positioned so as to have their surfaces in contact. The surfaces have a bonded portion and an unbonded portion therebetween. The unbonded portion has an elongated shape.

There is a first opening through the first member for communicating between the unbonded portion and the outside of the article. A second opening communicates between the unbonded portion and the inside of the article. The first and second openings are offset from each other.

The first and second openings and the unbonded portion define a normally open channel suitable for receiving an elongated filling means. At least the second member is sufficiently flexible to close the channel responsive to pressure from within a fluid fillable article which includes the valve.

In another aspect the invention comprises a self sealing fluid fillable article. The article comprises a fluid fillable member and the self sealing valve. The first planar member of the valve can be bonded directly to the fluid fillable member so as to close an aperture therein and to position the valve on the inside of the fluid fillable member. Alternatively, the first planar member of the valve can be bonded to a valve support member. The valve support member has an opening which is positioned to coincide with the opening in the first planar member. The valve support member is then bonded to the fluid fillable member so as to close an aperture therein and to locate the valve on the inside of the fluid fillable member.

In still another aspect the invention comprises a method for forming a self sealing valve. The method comprises, generally speaking, providing first and second planar members and bonding them together. The members are bonded in such a way as to result in both bonded and unbonded areas therebetween. The unbonded portion is elongated and may be totally surrounded by the bonded portion. Alternatively, the unbonded portion can extend to the edge of the valve in at least one location.

A first opening is formed in the first planar member for communicating between the unbonded portion and the outside of a fluid fillable article containing the valve. In embodiments where the unbonded portion does not extend to the edge of the valve, a second opening is formed in the second member. The first and second openings are offset from one another.

BRIEF DESCRIPTION OF THE DRAWINGS

The invention will now be described with reference to the drawings in which.

All of the figures are cross-sectional schematics.

DETAILED DESCRIPTION

Figure 1:
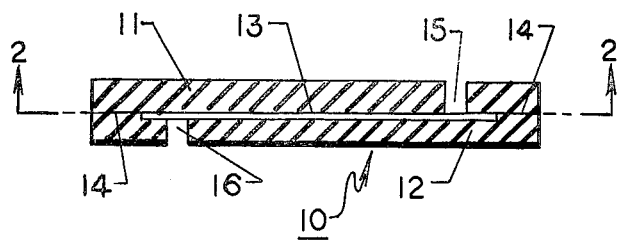
FIG. 1 shows a valve according to the present invention.

Referring more specifically to FIG. 1 there is shown valve 10 which includes first and second planar members 11 and 12, respectively.

Members 11 and 12 are bonded so as to provide unbonded portion 13 and bonded portion 14.

First opening 15 through first planar member 11 and second opening 16 through second planar member 12 are offset from one another. Both openings communicate with unbonded portion 13.

Openings 15 and 16 and unbonded portion 13 define a normally open channel suitable for receiving an elongated filler means such as a tube.

First and second planar members 11 and 12 can be made from any useful material. To be useful, the material should be sufficiently flexible to expand and to form a channel between first opening 15 and second opening 16 when a filler means is inserted (see FIG. 4). The material for at least second member 12 should be sufficiently flexible to close unbonded area 13 responsive to pressure, such as pressure from within a mammary prosthesis.

When valve 10 is used in a mammary prosthesis, it may be desirable to form first and second members 11 and 12 from a soft material which is not readily palpable after surgical implantation.

First and second members 11 and 12 should be formed from a material which is readily bondable.

Any such material is suitable for use in the present invention. Especially satisfactory results have been observed when silicone rubbers are used. Silicone rubber is not readily palpable after implantation, and it is sufficiently flexible to close unbonded area 13 responsive to pressure against member 12.

Silicone rubber also has an advantage of easy bonding. A valve is assembled from pieces of uncured material. After assembly, the valve is heat cured to set the rubber and, at the same time, to accomplish bonding in the desired areas without the use of adhesives. Bonding is avoided in selected areas, such as unbonded portion 13, by the application of a release agent prior to heat curing. A dry powder release agent such as Vydax-A.R. (commercially available from Osborn-Chicago Manufacturing Company) is typically used.

An additional advantage of silicone rubber for constructing the valve of the present invention is the ease with which such a valve can be attached to a fluid fillable member, such as a mammary prosthesis. The valve can be bonded directly to the article using a medical grade adhesive (see FIG. 5). Alternatively, the valve can be bonded by heat curing to a valve support member (see FIG. 6), which is usually bonded at the same time to the fluid fillable member (see FIG. 7).

Figure 2:
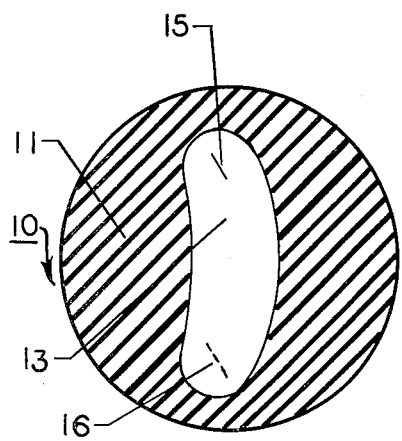
FIG. 2 shows the valve of FIG. 1 along line 2—2 thereof.

Referring more specifically to FIG. 2, there is shown valve 10 which is a top view of valve 10 of FIG. 1 along lines 2—2.

First flexible member 11 is bonded to a second flexible member except in unbonded area 13. First opening 15 in first member 11 communicates between unbonded area 13 and the outside of an inflatable article containing the valve. Second opening 16 is in the second flexible member which lies behind first flexible member 11. Openings 15 and 16 are offset.

Openings 15 and 16 and unbonded area 13 form a normally open channel for receiving an elongated filler tube. It is noted that unbonded portion 13 is non-linear.

Figure 3:
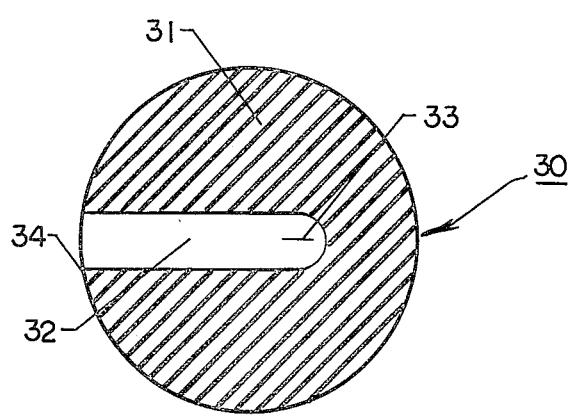
FIG. 3 shows a modification of the valve of FIGS. 1 and 2 wherein the unbonded portion extends to the edge of the valve.

Referring more specifically to FIG. 3 there is shown valve 30, which is another embodiment of the present invention.

First flexible member 31 is bonded to a second flexible member, which lies behind it, except in unbonded area 32. First opening 33 in first flexible member 31 communicates between unbonded area 32 and the area outside an article containing the valve.

Unbonded area 32 extends to the edge of valve 30 to form a second opening 34 in the edge between first flexible member 31 and the second flexible member. Second opening 34, first opening 33 and unbonded portion 32 form a normally open channel suitable for receiving an elongated filler means (e.g. see FIG. 4).

Figure 4:
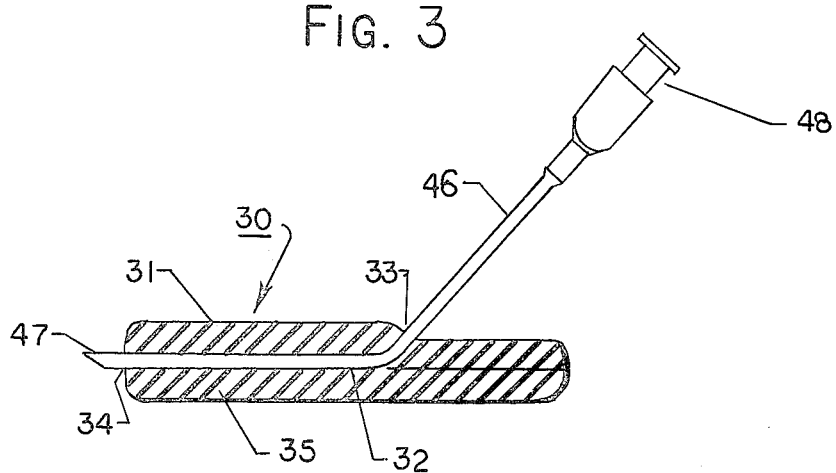
FIG. 4 shows the valve of FIG. 3 in which a filling tube has opened the channel.

Referring more specifically to FIG. 4 there is shown valve 30 of FIG. 3 in which a filling tube has opened the channel. First flexible member 31 and second flexible member 35 are bonded together except in unbonded portion 32.

First opening 33 in first flexible member 31 communicates between unbonded portion 32 and an area outside an article containing the valve. Second opening 34 is in the edge of the valve between members 31 and 35. Opening 34 is formed by an extension of unbonded area 32 to the edge of the valve.

Openings 33 and 34 and unbonded portion 32 form a channel which is suitable to receive filler tube 46. Tube 46 is typical of a variety of elongated filler means which are used to fill articles such as mammary prostheses. Tube 46 has an angle-cut lead end 47 for easy passage through opening 33 and unbonded area 32. Internally threaded end 48 enables easy attachment of tube 46 to a source of fluid.

Figure 5:
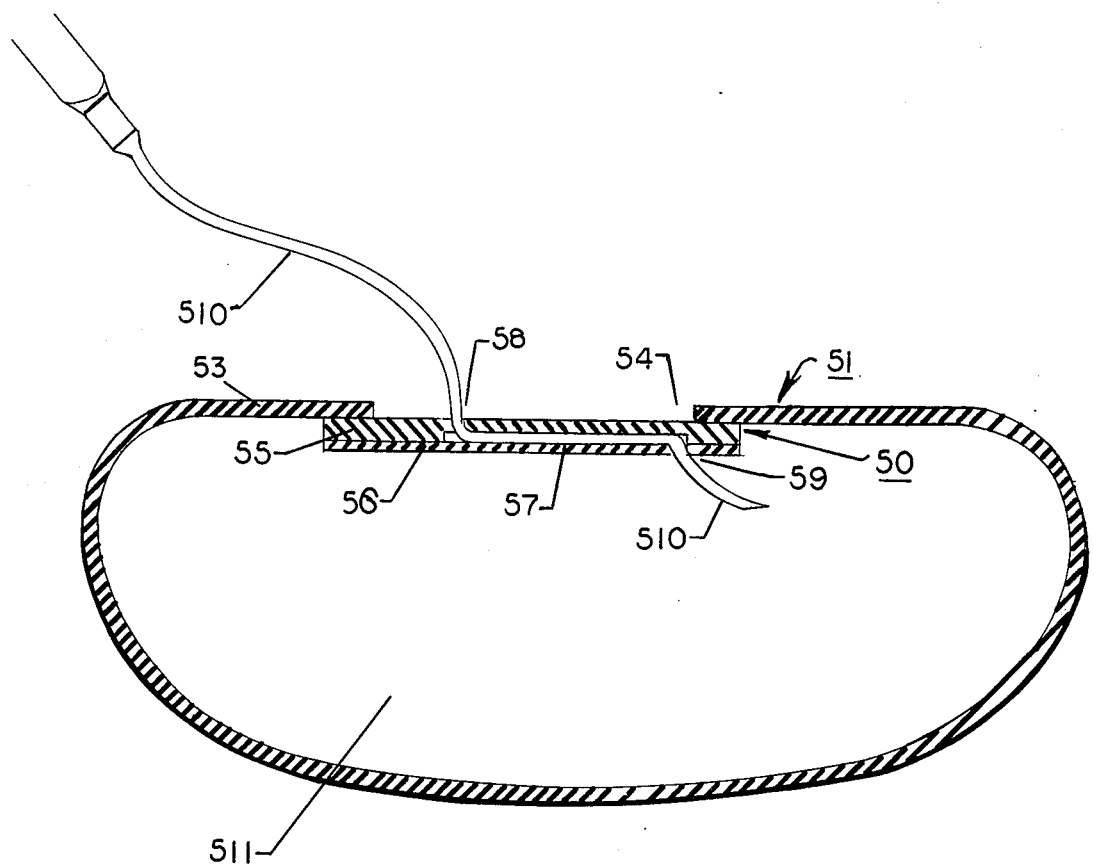
FIG. 5 shows the valve of FIG. 1 as a part of a self sealing mammary prosthesis.

Referring more specifically to FIG. 5 there is shown a valve 50 according to the present invention as a part of a mammary prosthesis 51. Valve 50 is bonded to prosthesis sac 53 to close an aperture 54 therein.

Valve 50 includes first and second flexible members 55 and 56 which are bonded together except at unbonded portion 57. Opening 58 in first flexible member 55 and opening 59 in second flexible member 56 are offset from one another. Both openings communicate with unbonded area 57 to form a channel for filler tube 510.

Fluid 511 for filling prosthesis 51 is supplied through tube 510. When tube 510 is removed, pressure from fluid 511 on second flexible member 56 collapses unbonded portion 57 sufficiently to avoid the passage of fluid 511.

Figure 6:
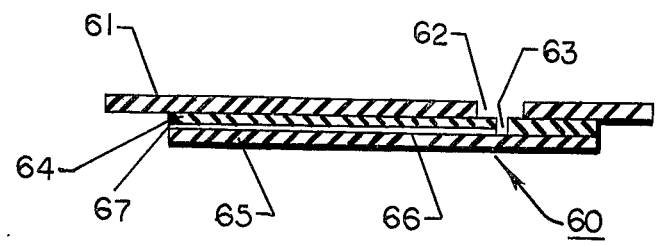
FIG. 6 shows a valve bonded to a valve support member.

Referring more specifically to FIG. 6 there is shown valve 60 according to the present invention mounted on a flexible support member 61. Support member 61 includes aperture 62 which is positioned to correspond with the position of first opening 63 in first flexible member 64.

First flexible member 64 and second flexible member 65 are bonded together except at unbonded portion 66. Unbonded portion 66 extends to the edge of valve 60 to form second opening 67.

Figure 7:
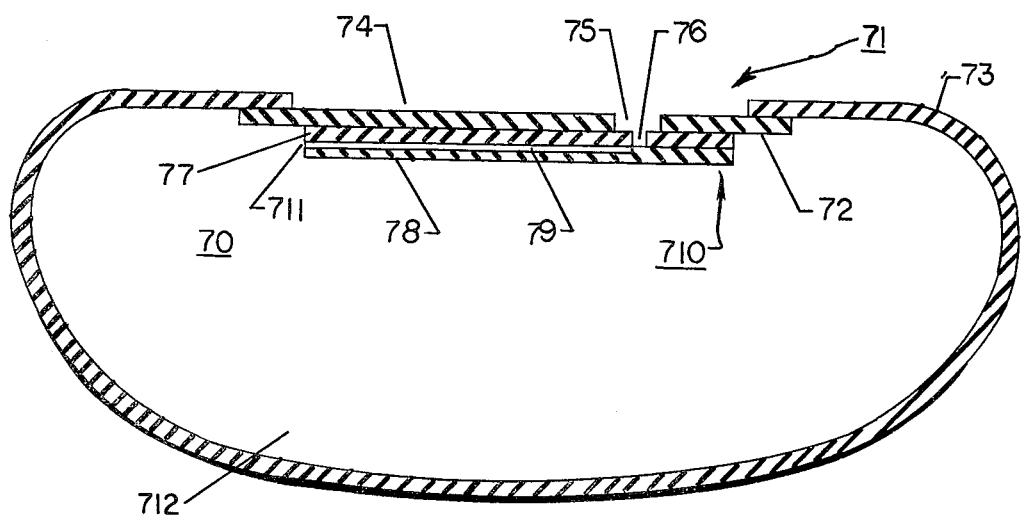
FIG. 7 shows the valve of FIG. 6 as a part of a self sealing mammary prosthesis.

Referring more specifically to FIG. 7 there is shown a valve and valve support member assembly 70 positioned in a fluid fillable article 71.

Valve support member 72 is bonded to sac 73 to close aperture 74 therein.

Opening 75 in support member 72 coincides with first opening 76 in first flexible member 77. First flexible member 77 is bonded to second flexible member 78 except at unbonded portion 79. Unbonded portion 79 extends to the edge of valve 710 to form opening 711.

Fluid 712 exerts a sufficient pressure against second flexible member 78 to close unbonded portion 79 so that fluid 712 remains in fluid fillable article 71.

Figure 8:
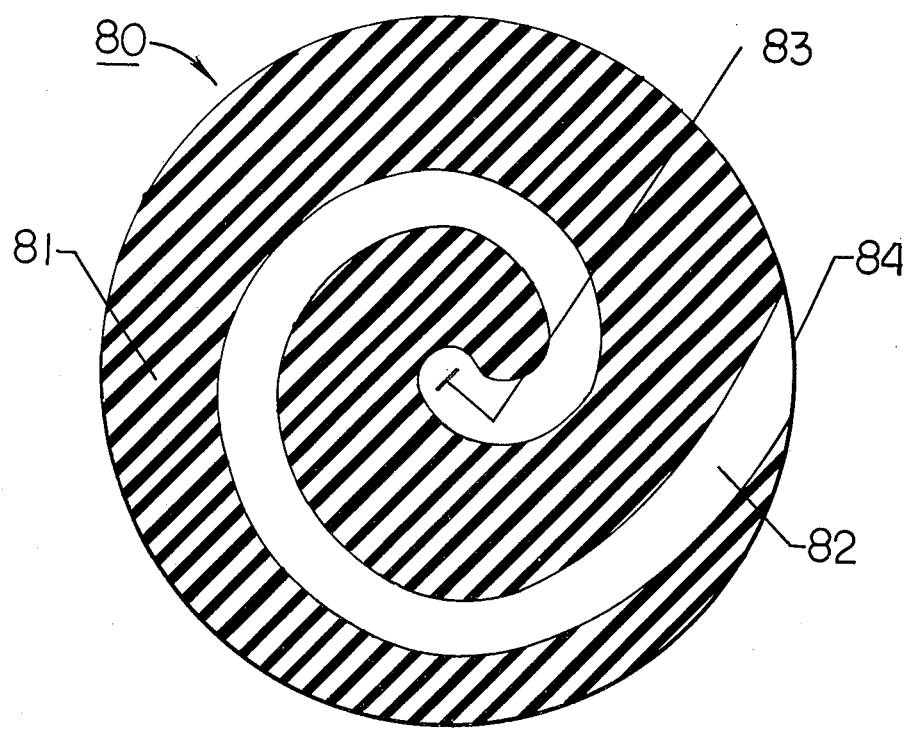
FIG. 8 shows a valve according to the present invention wherein the unbonded portion is non-linear.

Referring more specifically to FIG. 8 there is shown valve 80 which includes first flexible member 81. Member 81 is bonded to a second flexible member, which lies behind it, except at unbonded area 82. Unbonded area 82 has a non-linear shape which creates a curled normally open channel between first opening 83 in member 81 and second opening 84 at the edge of the valve. The non-linear shape of unbonded area 82 provided greater surface area for sealing off the fluid path. The valve configuration of FIG. 8 is often useful in fluid fillable articles which may have low fluid pressures.

The invention is described below by way of example.

EXAMPLE 1

Valves according to the present invention are formed in the design of FIG. 3 using flexible members of 0.010 inch (0.0254 mm) thick uncured silicone rubbers of various types. Pairs of members are selected from stocks of mechanical grade, clean grade and medical grade silicone rubbers.

Vydax-A.R., a dry powder release agent is placed on one of each of the pairs of members in the shape of the area which is to be unbonded. The release agent is placed so as to result in an unbonded area substantially as shown in FIG. 3. The other flexible member of each pair is placed over the first member and the members are pressed together with a total force of 20,000 lb/in$^2$ at a temperature of 160° C. for 15 minutes.

The channels in the cured valves are opened with a filler tube for examination.

In such sample, support member (item 61 of FIG. 6) of uncured (tacky) silicone rubber is placed over the valve so that the valve sticks to the support member. A hole in the support member corresponds to the opening in the first surface of the valve. The end of a pencil-like tool is used to pick up the valve and support member by means of the support member's tackiness. Opposite sides of the valve and support member assembly are curled slightly with the fingers while supported on the tool so as to reduce its diameter in one dimension. A mammary envelope made of cured silicone rubber is partially inflated by blowing into it, and the assembly is inserted into the envelope through the aperture. The valve support member is larger in diameter than the aperture, but the slight curling of the edges enables insertion of the assembly through the aperture. After insertion the member is uncurled and the tool is used to position the assembly and to draw it against the envelope around the edges of the aperture where it sticks because of its tackiness. The tool is then removed from the support member.

The valves and the mammary envelopes are bonded to either side of the support member by heat curing to form a construction such as that shown in FIG. 7. The mechanical grade silicone rubber valve assembly is cured for 40 minutes at 160° C. The clean grade valve assembly is cured for 30 minutes at 160° C., and the medical grade valve is cured at 300° C. for 15 minutes.

The prostheses are filled about 170 full of sterile water and a 500 g weight is placed on each construction. After 24 hours the 500 g force is released and each prosthesis and valve is inspected for leakage. The prostheses and valves contained therein are observed not to leak.

The valves made with mechanical grade and clean grade silicone rubber are found to have good bonding in the desired areas and no bonding in the area treated with a release agent. The line between the bonded and unbonded areas is regular. In the valve made with medical grade silicone rubber, bonding is not uniform and the line between the bonded and unbonded portions is irregular.

EXAMPLE 2

A fluid fillable mammary prosthesis is made according to the procedure of Example 1 wherein clean grade silicone rubber is used to make the valve.

The prosthesis is filled with a silicone gel (available from Dow Corning Corporation under the designation Dow Corning Q7-2167/Q7-2168 Silicone Gel System) to a pressure of 30 cm. HOH. A filler tube such as that shown in FIGS. 4 and 5 is used. When the filler tube is withdrawn, the valve is seen to seal the prosthesis without leakage. The valve is not readily palpable from the front of the prosthesis.

EXAMPLE 3

A valve of Example 1 made with medical grade silicone rubber is placed directly in a mammary prosthesis sac (as in FIG. 5). The valve is bonded directly to the mammary envelope using SILASTIC ® Medical Adhesive-Silicone Type A medical adhesive. After assembly and curing, the prosthesis is filled with a gel as in Example 2 with similar results.

The present invention has been disclosed in the above teachings, drawings and examples with sufficient clarity and conciseness to enable one skilled in the art to make and use the invention, to know the best mode for carrying out the invention to distinguish it from other inventions and from what is old. Many variations and obvious adaptations of the inventions will readily come to mind, and these are intended to be contained within the scope of the invention as claimed below.

What is claimed is:

1. A valve for use in a fluid fillable article, the valve comprising:
   (a) first and second planar members positioned to have their surfaces in contact, the surfaces having a major bonded portion and an minor unbonded portion of elongated shape therebetween;

(b) a first opening through the first member for communicating between the unbonded portion and the outside of a fluid fillable article; and (c) a second opening for communicating between the inside of a fluid fillable article and the unbonded portion, the second opening being offset from the position of the first opening;

the first and second openings and the unbonded portion defining a normally open channel suitable for receiving an elongated filling means and at least the second member having sufficient flexibility to close the channel responsive to pressure from within a fluid fillable article which contains the valve.

2. The valve of claim 1 wherein the second opening is positioned along the edge of the valve.

3. The valve of claim 1 wherein the second opening is in the second member.

4. The valve of claim 1 wherein the members are formed from a material comprising a silicone rubber and wherein bonded portions are bonded by heat curing.

5. The valve of claim 1 wherein the unbonded portion has a non-linear shape.

6. The valve of claim 1 wherein the first member is bonded to a planar valve support, the valve support having an opening positioned to coincide with the opening in the first member.

7. The valve of claim 6 wherein at least the first member and the valve support are formed from a material comprising a silicone rubber and wherein bonding is by heat curing.

8. The valve of claim 6 wherein the valve support is bonded to a fluid fillable article so as to close an aperture therein and to position the valve on the inside of the article.

9. The valve of claim 8 wherein at least the valve support and the fluid article are formed from a material comprising a silicone rubber and wherein bonding is by heat curing.

10. The valve of claim 8 wherein the fluid fillable article is a mammary prosthesis.

11. The valve of claim 1 wherein the first planar member is bonded to a fluid fillable article so as to close an aperture therein and to position the valve on the inside of the inflatable article.

12. The valve of claim 11 wherein bonding between the first planar member and the fluid fillable article is by an adhesive.

13. The valve of claim 11 wherein the inflatable article is a mammary prosthesis.

14. A self-sealing fluid fillable article comprising a fluid fillable member and a valve, the valve comprising:

(a) first and second planar flexible members positioned to have their surfaces in contact, the surfaces having a major bonded portion and an minor unbonded portion of extended shape therebetween;

(b) a first opening through the first member for communicating between the unbonded portion and the outside of the fluid fillable article; and (c) a second opening for communicating between the inside of the fluid fillable article and the unbonded portion, the second opening being offset from the position of the first opening, the first and second openings and the unbonded portion defining a normally open channel for receiving an elongated filling means;

at least the second member having sufficient flexibility to close the channel responsive to pressure from within the fluid fillable article.

15. The self-sealing fluid fillable article of claim 14 wherein at least the first planar member and the fluid fillable member are formed from a material comprising a silicone rubber.

16. The self-sealing fluid fillable article of claim 14 further including a planar valve support member bonded on one side to the first planar member and on the other side to the fluid fillable member, the valve support member having an opening positioned to coincide with the opening in the first member.

17. The self-sealing fluid fillable article of claim 14 wherein the fluid fillable member is a mammary prosthesis.

* * * * *

UNITED STATES PATENT AND TRADEMARK OFFICE
CERTIFICATE OF CORRECTION

PATENT NO. : 4,263,682
DATED : April 28, 1981
INVENTOR(S) : Mark A. Bejarano

It is certified that error appears in the above-identified patent and that said Letters Patent are hereby corrected as shown below:

Column 5, line 36, "provided" should read --provides--.

Column 6, line 19, "170" should read --2/3--.

Signed and Sealed this

Twenty-ninth Day of December 1981

[SEAL]

Attest:

GERALD J. MOSSINGHOFF

*Attesting Officer*   *Commissioner of Patents and Trademarks*